United States Patent
Kitamura et al.

(10) Patent No.: US 9,682,866 B2
(45) Date of Patent: Jun. 20, 2017

(54) NEUTRAL COMPLEX OF CYCLIC SILANE, MANUFACTURING METHOD THEREFOR, AND METHOD FOR MANUFACTURING CYCLIC HYDROGENATED SILANE OR CYCLIC ORGANIC SILANE

(71) Applicant: NIPPON SHOKUBAI CO., LTD., Osaka (JP)

(72) Inventors: Morihiro Kitamura, Osaka (JP); Shin-ya Imoto, Hyogo (JP); Tomonori Shinokura, Osaka (JP); Takashi Abe, Osaka (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/105,190

(22) PCT Filed: Dec. 19, 2014

(86) PCT No.: PCT/JP2014/083681
§ 371 (c)(1),
(2) Date: Jun. 16, 2016

(87) PCT Pub. No.: WO2015/093592
PCT Pub. Date: Jun. 25, 2015

(65) Prior Publication Data
US 2016/0311692 A1   Oct. 27, 2016

(30) Foreign Application Priority Data
Dec. 20, 2013  (JP) .................................. 2013-264515
Dec. 20, 2013  (JP) .................................. 2013-264516

(51) Int. Cl.
| | | |
|---|---|---|
| C01B 33/107 | (2006.01) | |
| C07F 9/50 | (2006.01) | |
| C09D 1/00 | (2006.01) | |
| C01B 33/04 | (2006.01) | |
| C07F 7/21 | (2006.01) | |

(52) U.S. Cl.
CPC ........ C01B 33/10773 (2013.01); C01B 33/04 (2013.01); C07F 7/21 (2013.01); C07F 9/5022 (2013.01); C09D 1/00 (2013.01)

(58) Field of Classification Search
CPC ..... C01B 33/10773; C01B 33/04; C07F 7/21; C07F 9/5022; C09D 1/00
USPC ........................................................ 556/400
See application file for complete search history.

(56) References Cited

U.S. PATENT DOCUMENTS

| | | | |
|---|---|---|---|
| 5,942,637 A * | 8/1999 | Boudjouk | C07F 7/025 423/341 |
| 2002/0076378 A1 | 6/2002 | Wolfe et al. | |
| 2014/0012029 A1 | 1/2014 | Abe et al. | |
| 2014/0012030 A1 | 1/2014 | Abe et al. | |
| 2014/0219893 A1 | 8/2014 | Imoto et al. | |

FOREIGN PATENT DOCUMENTS

| | | |
|---|---|---|
| JP | 4519955 | 8/2010 |
| JP | 2013-203601 | 10/2013 |
| JP | 2014-12648 | 1/2014 |
| JP | 2014-141398 | 8/2014 |

OTHER PUBLICATIONS

International Search Report issued Mar. 10, 2015 in corresponding (PCT) Application No. PCT/JP2014/083681.
Dai et al., "Inverse Sandwich" Complexes of Perhalogenated Cyclohexasilane, Organometallics, vol. 29, No. 10, 2010, pp. 2203-2205.
Dai et at, Coordination chemistry of $Si_5Cl_{10}$ with organocyanides, Dalton Transactions, vol. 39, No. 46, 2010, pp. 11188-11192.
Hengge et al., Preparation of Cyclohexasilane, $Si_6H_{12}$, Angew. Chem. Int. Ed. Engl., vol. 16, No. 6, 1977, p. 403.

* cited by examiner

*Primary Examiner* — Porfirio Nazario Gonzalez
(74) *Attorney, Agent, or Firm* — Wenderoth, Lind & Ponack, L.L.P.

(57) ABSTRACT

A neutral complex of a cyclic silane characterized in being represented by the general formula $[Y]_1[Si_mZ_{2m-a}H_a]$. (In the formula: Y is at least one kind of coordination compound selected from a group consisting of (1) compounds represented as $X^1R^1_n$. (when $X^1$ is P, P=O or N, n=3 and each $R^1$ represents a substituted or unsubstituted alkyl group or aryl group and $R^1$s are the same or different; when $X^1$ is S, S=O or O, n=2 and each $R^1$ represents the same group as described above and $R^1$s are the same or different; and the number of amino groups in $X^1R^1_n$ is 0 or 1), and (2) at least one heterocyclic compound selected from the group consisting of substituted or unsubstituted N—, O—, S —or P— containing heterocyclic compounds that have an unshared electron pair in the ring (the number of amino groups in the heterocyclic compound is 0 or 1), each Z represents a halogen atom of any of Cl, Br, I and F and Zs are the same or different, l is 1 or 2, m is 3 to 8, and a is 0 to m.

13 Claims, 4 Drawing Sheets

NEUTRAL COMPLEX OF CYCLIC SILANE, MANUFACTURING METHOD THEREFOR, AND METHOD FOR MANUFACTURING CYCLIC HYDROGENATED SILANE OR CYCLIC ORGANIC SILANE

TECHNICAL FIELD

The present invention relates to a neutral complex of a cyclic silane, a method for manufacturing the neutral complex of cyclic silane, and a method for efficiently manufacturing a cyclic hydrogenated silane such as cyclohexasilane or a cyclic organic silane from the neutral complex of cyclic silane, without generating silane gas or an organic monosilane, or with only a small amount of silane gas or an organic monosilane generated.

BACKGROUND ART

A silicon thin film is used for applications such as solar cells and semiconductors, and this silicon thin film has been previously prepared by a vapor deposition film-forming method (CVD method) using monosilane as a raw material. Recently, in place of the CVD method, a new production method using cyclic hydrogenated silane has been focused. This production method is a coating film-forming method (liquid process) in which a hydrogenated polysilane solution is applied to a substrate, followed by calcination, and cyclopentasilane is used as a raw material for the preparation of the hydrogenated polysilane solution. Cyclopentasilane is commercially available, and has been reported to be hydrogenated polysilane by UV irradiation (Non-Patent Document 1). However, cyclopentasilane requires multistep synthesis using an expensive water-reactive reagent and a purification step for its production, and thus is very expensive.

Therefore, the present inventors have focused on cyclohexasilane as an alternate material for cyclopentasilane. As the synthesis method of a cyclohexasilane, Hengge et at report that a cyclohexasilane can be synthesized using diphenyldichlorosilane as a starting material (Non-Patent Document 1).

PRIOR ART DOCUMENTS

Non-Patent Documents

Non-Patent Document 1: Edwin Hengge and Dieter Kovar, "Preparation of Cyclohexasilane", Angew. Chem. Ed. Engl. 16(1977) No. 6, p. 403

SUMMARY OF THE INVENTION

Problems to be Solved by the Invention

In the method described in Non-Patent Document 1, however, the amount of a reducing agent used is very large relative to that of a complex (13 equivalents in Non-Patent Document 1). This not only causes the increase in cost of raw materials, but also generates many by-products derived from the reducing agent so that a great amount of costs are further required for a treatment of making the by-products deactivated after the reaction. In addition, the method described in Non-Patent Document 1 cannot be said to provide a high yield of a cyclohexasilane.

The present invention was made by focusing on such circumstances, and an object thereof is to provide a neutral complex of a cyclic silane, which can be used as an intermediate that can give a cyclic hydrogenated silane or a cyclic organic silane by a homogeneous reaction in a solution state or a reaction in a suspension high in dispersibility, while suppressing the production of by-products such as silane gas and organic monosilane in a reduction step. Another object of the present invention is to provide a method for manufacturing a neutral complex of a cyclic silane and a method for manufacturing a cyclic hydrogenated silane or a cyclic organic silane from the neutral complex of a cyclic silane, and also to reduce costs of raw materials accounting for the manufacturing costs and costs of removing by-products after a reaction, without impairing the yield of the cyclic hydrogenated silane even when the amount of a reducing agent is decreased.

Solutions to the Problems

As a result of repetitive earnest studies to achieve the objects, the present inventors succeeded in manufacturing a neutral complex of a cyclic silane having excellent solubility in a solvent by cyclizing a halosilane compound in the presence of a special coordination compound. As a result, this cyclization reaction, or a subsequent reduction step or alkylation or arylation step can be conducted by a homogeneous reaction in a solution state or a reaction in a suspension high in dispersibility. This neutral complex of a cyclic silane can be converted to a cyclic hydrogenated silane when subjected to reduction, without generating silane gas, or with only a small amount of silane gas generated. Similarly, when subjected to alkylation or arylation, the neutral complex of a cyclic silane can also be converted to a cyclic organic silane while suppressing the production of organic monosilane as a by-product.

A neutral complex of a cyclic silane of the present invention, represented by the general formula $[Y]_1[Si_m Z_{2m-a} H_a]$, wherein Y is at least one coordination compound selected from the group consisting of (1) a compound represented as $X^1 R^1_n$ (when $X^1$ is P, P=O or N, n=3 and each $R^1$ represents a substituted or unsubstituted alkyl group or aryl group and $R^1$s are the same or different; when $X^1$ is S, S=O or O, n=2 and each $R^1$ represents the same group as described above and $R^1$s are the same or different; and the number of amino groups in $X^1 R^1_n$ is 0 or 1), and (2) at least one heterocyclic compound selected from the group consisting of substituted or unsubstituted N—, O—, S— or P— containing heterocyclic compounds that have an unshared electron pair in the ring (the number of amino groups in the heterocyclic compound is 0 or 1), each Z represents a halogen atom of any of Cl, Br, I and F and Zs are the same or different, l is 1 or 2, m is 3 to 8, and a is 0 to m.

The neutral complex of a cyclic silane, wherein Y in the general formula is preferably at least one compound selected from the group consisting of $PR_3$ and a substituted or unsubstituted N-containing heterocyclic compound having an unshared electron pair in the ring. It is preferred that the neutral complex of a cyclic silane contains $[Y]_1[Si_6Cl12]$ (l is 1 or 2). It is preferred embodiment that the neutral complex of a cyclic silane is an intermediate for synthesizing a cyclic hydrogenated silane or a cyclic organic silane.

The present invention encompasses a method for manufacturing a neutral complex of a cyclic silane, comprising a step of conducting a cyclization reaction of a halosilane compound in the presence of at least one coordination compound selected from the group consisting of the following (3) and (4):

(3) compound represented as $X^2R^2_q$ (when $X^2$ is P or P=O, q=3 and each $R^2$ represents a substituted or unsubstituted alkyl group or aryl group and $R^2$s are the same or different; when $X^2$ is S, S=O or O, q=2 and each $R^2$ represents a substituted or unsubstituted alkyl group or aryl group and $R^2$s are the same or different; when $X^2$ is CN, q=1 and $R^2$ represents a substituted or unsubstituted alkyl group or aryl group; and the number of amino groups in $X^2R^2_q$ is 0 or 1); and (4) at least one heterocyclic compound selected from the group consisting of substituted or unsubstituted N—, O—, S— or P— containing heterocyclic compounds that have an unshared electron pair in the ring (the number of amino groups in the heterocyclic compound is 0 or 1).

The cyclization reaction is preferably conducted in the presence of a tertiary amine (except a tertiary polyamine) and the neutral complex of a cyclic silane contains a neutral complex of dodecachlorocyclohexasilane including the coordination compound(s) coordinated to dodecachlorocyclohexasilane.

The present invention encompasses a method for manufacturing a cyclic hydrogenated silane, comprising a step of reducing the neutral complex of a cyclic silane obtained in the manufacturing method. In the reduction step, at least one reducing agent selected from the group consisting of an aluminum-based reducing agent and a boron-based reducing agent is preferably used as a reducing agent. In the reduction step, embodiment the hydride equivalent in the reducing agent relative to one silicon-halogen bond in the neutral complex of a cyclic silane being 0.9 to 2.0 in the reduction step and embodiment the reduction step being conducted at −198° C. to −10° C. are preferably embodiments of the present invention. The present invention encompasses a method for manufacturing a cyclic organic silane, comprising a step of alkylating or arylating the neutral complex of a cyclic silane obtained by the manufacturing method with at least one reagent selected from the group consisting of a Grignard reagent and an organolithium reagent.

Effects of the Invention

The neutral complex of a cyclic silane of the present invention allows, for its excellent solubility in a solvent or excellent affinity to a solvent, a reaction in a homogeneous solution system or in a suspension high in dispersibility in a cyclization reaction for obtaining the neutral complex of a cyclic silane and when the resultant neutral complex of a cyclic silane is subjected to reduction, alkylation or arylation. Therefore, the method for manufacturing a neutral complex of a cyclic silane of the present invention is industrially useful. Further, silane gas and organic monosilane are not generated, or only small amounts of silane gas and organic monosilane are generated. Therefore, a combustion facility and an adsorption facility as countermeasures against silane gas and organic monosilane, which have conventionally been used in the production of a cyclic hydrogenated silane or a cyclic organic silane, can be eliminated, and a countermeasure of dilution of the generated gas with inert gas or a simple device such as a scrubber is sufficient. Thus, a cyclic hydrogenated silane and a cyclic organic silane can be efficiently produced with a simple device. In addition, the amount of a reducing agent when the neutral complex of a cyclic silane can be reduced, resulting in a great decrease in raw material costs and costs for a treatment of making the by-products deactivated. Further, production of a cyclic hydrogenated silane at a low temperature enables suppression of decomposition or polymerization of an intermediate product or an object product, resulting in improvement of a yield.

MODE FOR CARRYING OUT THE INVENTION

Figure 1:
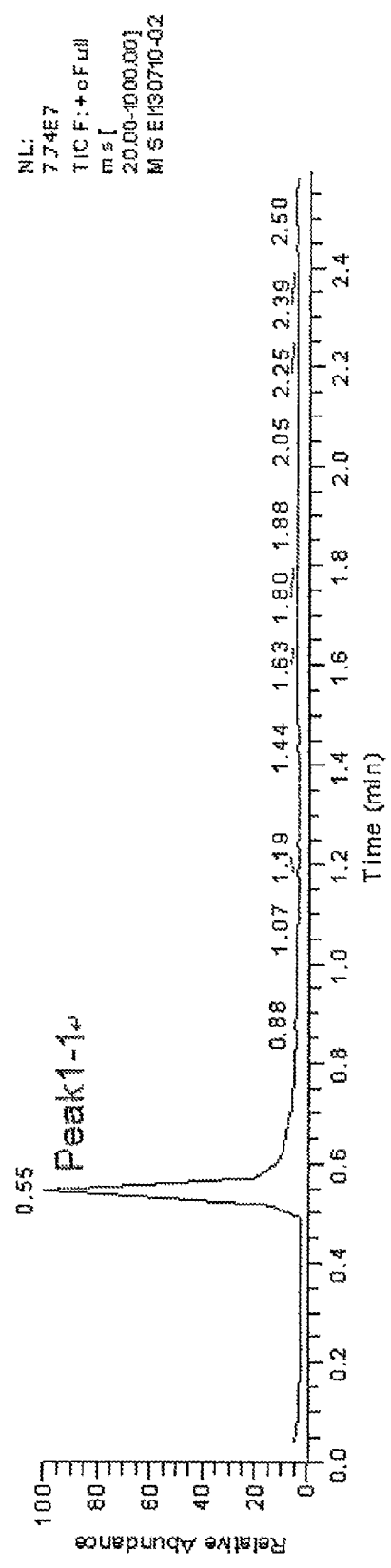
FIG. 1 shows a mass spectrometry result of a neutral complex of a cyclic silane obtained in Example 1.

The neutral complex of a cyclic silane of the present invention includes 2 patterns.

[Neutral Complex of Cyclic Silane of Pattern 1]

The neutral complex of a cyclic silane of the pattern 1 is represented by the following general formula.

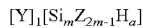

$[Y]_l[Si_mZ_{2m-l}H_a]$ (wherein Y is at least one coordination compound selected from the group consisting of (1) a compound represented as $X^1R^1_n$ (when $X^1$ is P, P=O or N, n=3 and each $R^1$ represents a substituted or unsubstituted alkyl group or aryl group and $R^1$s are the same or different; when $X^1$ is S, S=O or O, n=2 and each $R^1$ represents the same group as described above and $R^1$s are the same or different; and the number of amino groups in $X^1R^1_n$ is 0 or 1), and (2) at least one heterocyclic compound selected from the group consisting of substituted or unsubstituted N—, O—, S— or P— containing heterocyclic compounds that have an unshared electron pair in the ring (the number of amino groups in the heterocyclic compound is 0 or 1), each Z represents a halogen atom of any of Cl, Br, I and F and Zs are the same or different, l is 1 or 2, m is 3 to 8, and a is 0 to m.)

This neutral complex of a cyclic silane is a complex containing a ring in which 3 to 8 (preferably 5 or 6, particularly 6) silicon atoms of a halosilane compound as a raw material are linked to one another. Therefore, m is 3 to 8, preferably 5 or 6, particularly preferably 6. In this neutral complex of a cyclic silane, not all the Si atoms are necessarily halogenated, and H atom may be bonded to a part of or all the Si atoms. When the number of H atoms is represented by a, the number of Z atoms is represented by 2m-a. The number of H atoms is theoretically 0 to 2m-1, preferably 0 to m. That is, when a is not less than m, the compound may be a compound in which H atoms are bonded to all the Si atoms.

As the raw material halosilane compound, for example, trihalogenated silanes such as trichlorosilane, tribromosilane, triiodosilane and trifluorosilane; dihalogenated silanes such as dichlorosilane, dibromosilane, diiodosilane and difluorosilane; and tetrahalogenated silanes such as tetrachlorosilane, tetrabromosilane, tetraiodosilane and tetrafluorosilane can be used. Accordingly, each Z represents a halogen atom of any of Cl, Br, I and F and Zs are the same or different. Among these halosilane compounds, a trihalogenated silane is preferred, and trichlorosilane is particularly preferred.

The neutral complex of a cyclic silane of the present invention is, as described below, one obtained by cyclizing a halosilane compound in the presence of a specific coordination compound. A product containing this neutral complex of a cyclic silane is an intermediate that is converted to a cyclic hydrogenated silane by reduction, or an intermediate that is converted to a cyclic organic silane by a Grignard reagent or an organolithium reagent.

Next, a ligand Y in the neutral complex of a cyclic silane of the pattern 1 is described.

Y in the neutral complex of a cyclic silane of the pattern 1 is at least one coordination compound selected from the group consisting of (1) a compound represented as $X^1R^1_n$ (when $X^1$ is P, P=O or N, n=3 and each $R^1$ represents a substituted or unsubstituted alkyl group or aryl group and $R^1$s are the same or different; when $X^1$ is S, S=O or O, n=2 and each $R^1$ represents the same group as described above and $R^1$s are the same or different; and the number of amino groups in $X^1R^1_n$ is 0 or 1), and (2) at least one heterocyclic compound selected from the group consisting of substituted or unsubstituted N—, O—, S— or P— containing heterocyclic compounds that have an unshared electron pair in the ring (the number of amino groups in the heterocyclic compound is 0 or 1). The number of Y coordinated to a cyclic silane is 1 and l is 1 or 2.

In $X^1R^1_n$ (1), $X^1$ is coordinated to a cyclic silane to form a neutral complex. When $X^1$ is P and P=O, $X^1$ is trivalent, and n representing the number of $R^1$s is 3. Each $R^1$ represents a substituted or unsubstituted alkyl group or aryl group and $R^1$s are the same or different. $R^1$ is more preferably a substituted or unsubstituted aryl group. Examples of $R^1$ as the alkyl group include linear, branched or cyclic alkyl groups, and preferable examples thereof include alkyl groups having 1 to 16 carbon atoms, such as a methyl group, an ethyl group, a propyl group, a butyl group, a pentyl group, a hexyl group, a heptyl group, an octyl group and a cyclohexyl group. Preferable examples of $R^1$ as the aryl group include aryl groups having about 6 to 18 carbon atoms, such as a phenyl group and a naphthyl group.

When $X^1$ is N, $X^1$ is trivalent, and n representing the number of $R^1$s is 3. Each $R^1$ represents a substituted or unsubstituted alkyl group or aryl group and $R^1$s are the same or different. $R^1$ is more preferably an unsubstituted alkyl group. Examples of $R^1$ as the alkyl group include linear, branched or cyclic alkyl groups, and preferable examples thereof include alkyl groups having 1 to 16 carbon atoms, among that, preferable examples thereof include alkyl groups having 1 to 4 carbon atoms, such as a methyl group, an ethyl group, a propyl group and a butyl group, more preferable examples thereof include alkyl groups having 1 to 3 carbon atoms. Preferable examples of $R^1$ as the aryl group include aryl groups having about 6 to 18 carbon atoms, such as a phenyl group and a naphthyl group.

When $X^1$ is P, P=O, or N, the substituent that may be possessed by the alkyl group is, for example, an alkoxy group, an amino group, a cyano group, a carbonyl group and a sulfonyl group, and the substituent that may be possessed by the aryl group is, for example, an alkoxy group, an amino group, a cyano group, a carbonyl group and a sulfonyl group. Examples of the amino group include a dimethylamino group and a diethylamino group, and the number of the amino groups is not more than 1 in $X^1R^1_3$. This is intended to eliminate a tertiary polyamine, which inhibits the production of the neutral complex of a cyclic silane. In the meantime, 3 $R^1$s may be the same or different.

When $X^1$ is S, S=O, or O, $X^1$ is divalent, and n representing the number of $R^1$s is 2. $R^1$ is as defined above, represents a substituted or unsubstituted alkyl group or aryl group. $R^1$ is more preferably a substituted or unsubstituted aryl group.

Specific examples of $X^1R^1_n$ (1) include a compound in which X is P, P=O, or N, such as triphenylphosphine (PPh$_3$), triphenylphosphine oxide (Ph$_3$P=O), tris(4-methoxyphenyOphosphine (P(MeOPh)$_3$) and triphenylamine; and a compound in which X is S=O, such as dimethyl sulfoxide.

The heterocyclic compound (2) in the above general formula is required to have an unshared electron pair in the ring, and the unshared electron pair coordinates to a cyclic silane to form a neutral complex of the cyclic silane. Examples of such a heterocyclic compound include at least one substituted or unsubstituted N—, O—, S— or P— containing heterocyclic compound that has an unshared electron pair in the ring. The substituents that may be possessed by the heterocyclic compound are the same as the substituents that may be possessed by $R^1$ as an alkyl group or an aryl group. Examples of the heterocyclic compound include pyridines, oxazoles, thiazoles, thiophenes and furans, and specific examples include pyridine, tetrahydrothiophene and tetrahydrofuran.

Among these coordination compounds, a compound that is a liquid at a reaction temperature can also play a role of a solvent (a manufacturing method therefor is described below).

Next, a method for manufacturing the neutral complex of a cyclic silane is described.

The method for manufacturing a neutral complex of a cyclic silane of the present invention (hereinafter, referred to as the "method for manufacturing the neutral complex) includes a step of cyclizing a halosilane compound in the presence of a coordination compound. This step gives a neutral complex of a cyclic halogenated silane (neutral complex of a cyclic silane) of the pattern 2 that has a wider variety than those of the pattern 1. A product containing a neutral complex of a cyclic silane of this pattern 2 can be said to be, similarly to the neutral complex of a cyclic silane of the pattern 1, ntermediate that can be converted to a cyclic hydrogenated silane by reduction, or an intermediate that can be converted to a cyclic organic silane by a Grignard reagent or an organolithium reagent.

As the raw material halosilane compound, any of the compounds exemplified as the raw materials of the neutral complex of a cyclic silane of the pattern 1 can be used.

The coordination compound that can be used in the manufacturing method of the present invention (method for manufacturing the neutral complex of a cyclic silane of the pattern 2) is at least one compound selected from the group consisting of the following (3) and (4).

(3) compound represented as $X^2R^2_q$ (when $X^2$ is P or P=O, q=3 and each $R^2$ represents a substituted or unsubstituted alkyl group or aryl group and $R^2$s are the same or different; when $X^2$ is S, S=O or O, q=2 and each $R^2$ represents a substituted or unsubstituted alkyl group or aryl group and $R^2$s are the same or different; when $X^2$ is CN, q=1 and $R^2$ represents a substituted or unsubstituted alkyl group or aryl group; and the number of amino groups in $X^2R^2_q$ is 0 or 1); and (4) at least one heterocyclic compound selected from the group consisting of substituted or unsubstituted N—, O—, S— or P— containing heterocyclic compounds that have an unshared electron pair in the ring (the number of amino groups in the heterocyclic compound is 0 or 1).

In other words, in addition to the compounds exemplified as $X^1R^1_n$ (1), $X^2R^2_q$ (3) includes compounds in which $X^2$ is CN, q is 1 and $R^2$ is a substituted or unsubstituted alkyl group or aryl group. The number of amino groups in $X^2R^2_q$ is 0 or 1. $R^2$ and $R^1$ have the same meaning.

Specific examples of $X^2R^2_q$ (3) include a compound in which X is P, P=O, or N, such as triphenylphosphine (PPh$_3$), triphenylphosphine oxide (Ph$_3$P=O), and tris(4-methoxyphenyl)phosphine (P(MeOPh)$_3$); a compound in which X is S=O, such as dimethyl sulfoxide; and a compound in which X is CN, such as p-tolunitrile (it is said to be the p-metylbenzonitrile).

The heterocyclic compound defined in (4) is the same as the heterocyclic compound described in (2).

Among these coordination compounds, a compound that is a liquid at a reaction temperature can also play a role of a solvent.

The cyclization reaction of the halosilane compound is preferably conducted by adding a tertiary amine (except a tertiary polyamine). Thereby, produced hydrochloric acid can be neutralized. An example of a scheme in which trichlorosilane as the halosilane compound, triphenylphosphine (PPh$_3$) as the coordination compound, and N,N-diisopropylethylamine (DIPEA) as the tertiary amine are used is shown below. A complex containing 6-membered ring dodecachlorocyclohexasilane (neutral complex including triphenylphosphine coordinated to dodecachlorocyclohexasilane ([PPh$_3$]$_2$[Si$_6$Cl$_{12}$])) is synthesized. This is a neutral complex of a cyclic silane of the pattern 1, and can also be said to be a neutral complex of a cyclic silane of the pattern 2.

[Chemical Formula 1]

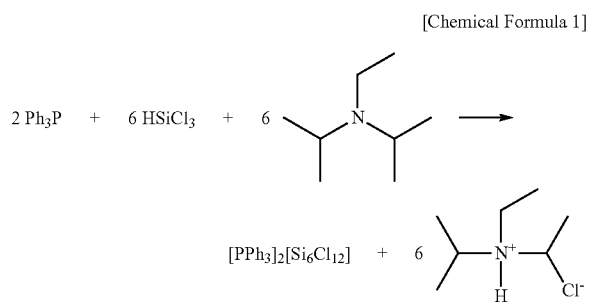

Preferable examples of the tertiary amine used in the cyclization reaction include triethylamine, tripropylamine, tributylamine, trioctylamine, triisobutylamine, triisopentylamine, diethylmethylamine, diisopropylethylamine (DIPEA), dimethylbutylamine, dimethyl-2-ethylhexylamine, diisopropyl-2-ethylhexylamine, methyldioctylamine, and the like. The tertiary amines may be used alone or in combination of two or more thereof. The tertiary amine also includes one that is coordinated to a cyclic silane, and amines that are comparatively low in volume and are high in symmetry, such as diethylmethylamine and triethylamine, are considered to be comparatively efficiently coordinated. However, only with a tertiary amine represented by $X^1R^1_n$ (1), the yield of the neutral complex of a cyclic silane tends to decrease, and therefore, any of the coordination compounds of (1) to (4) (a compound other than the tertiary amines represented by $X^1R^1_n$ (1)) is preferably used in combination.

The amounts of the coordination compound, the halosilane compound, and the tertiary amine to be used in the cyclization reaction may be appropriately determined. For example, when dodecachlorocyclohexasilane is synthesized as in the above scheme, a coordination compound in an amount of 2 mol is used relative to 6 mol of trichlorosilane. As another example, a coordination compound in an amount of 0.022 mol may be used relative to 0.133 mol trichlorosilane. The coordination compound can be used in an amount of at least 2 mol and can be used in an amount of up to about 50 mol relative to 6 mol of trichlorosilane. The tertiary amine is preferably used in an amount of 0.5 to 4 mol relative to 1 mole of trichlorosilane, and is particularly preferably used in the same number of mol as that of trichlorosilane. The same applies to the cases where other halosilane compounds are used.

The cyclization reaction can be conducted in an organic solvent as necessary. As the organic solvent, a solvent that does not prevent the cyclization reaction is preferred, and preferable examples thereof include halogenated hydrocarbon-based solvents (e.g. chloroform, dichloromethane and 1,2-dichloroethane), ether-based solvents (e.g. diethyl ether, tetrahydrofuran, cyclopentylmethyl ether, diisopropyl ether, and methyl tertiary-butyl ether) and aprotic polar solvents such as acetonitrile. Among these, chlorinated hydrocarbon-based solvents such as chloroform, dichloromethane and 1,2-dichloroethane are preferred, and 1,2-dichloroethane is particularly preferred. These organic solvents may be used alone or in combination of two or more thereof.

The amount of the organic solvent to be used is not particularly limited, but it is generally preferred to be adjusted so that the concentration of the halosilane compound is 0.5 to 10 mol/L, more preferably 0.8 to 8 mol/L, further preferably 1 to 5 mol/L.

The reaction temperature in the cyclization reaction step can be appropriately set according to the reactivity and is, for example, about 0 to 120° C., preferably about 15 to 70° C. Further, the cyclization reaction is recommended to be conducted in an atmosphere of inert gas such as nitrogen.

A solution of a neutral complex of a cyclic silane produced after the cyclization reaction may be condensed and washed with, for example, chloroform, dichloromethane, 1,2-dichloroethane, or acetonitrile to be purified. This neutral complex of a cyclic silane is a complex containing a ring in which 3 to 8 (preferably 5 or 6, particularly 6) silicon atoms of a halosilane compound as a raw material are linked to one another. For example, when trichlorosilane is used as a starting material, as in the above scheme, a complex containing 6-membered ring dodecachlorocyclohexasilane (neutral complex including triphenylphosphine coordinated to dodecachlorocyclohexasilane ([PPh$_3$]$_2$[Si$_6$Cl$_{12}$])) is generally produced. This neutral complex of a cyclic silane does not contain any silicon atom other than the silicon atoms that form the ring structure, and therefore, in the reduction, alkylation or arylation, silane gas and organic monosilane are not generated, or only small amounts of silane gas and organic monosilane are generated.

The yield and yield constant of the neutral complex of a cyclic silane produced in the cyclization reaction can be calculated by a methylation reaction represented by the following scheme, in which the complex reacts quantitatively.

[Chemical Formula 2]

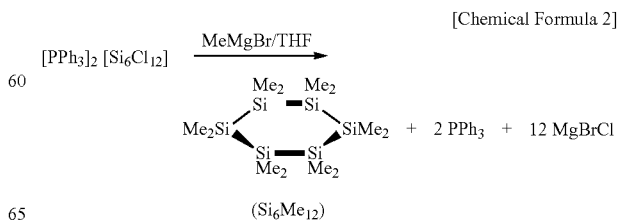

The production of the neutral complex of a cyclic silane of the pattern 1 is different from the method for manufacturing a neutral complex of a cyclic silane of the pattern 2 only in whether the compound used as a coordination compound is a compound exemplified as $X^1R^1_n$ (1) (pattern 1) or a compound exemplified as $X^2R^2_q$ (3) (pattern 2).

The neutral complex of a cyclic silane of the present invention can be produced as a solid of high purity by purification as described above. However, it can also be produced as a neutral complex composition of a cyclic silane containing impurities if desired. The neutral complex composition of a cyclic silane contains a neutral complex of a cyclic silane preferably in an amount of not less than 90% by mass, more preferably in an amount of not less than 95% by mass. The upper limit of the amount is, for example, 99.99% by mass, but may be 100% by mass. The impurities are, for example, a residue of a solvent or a coordination compound, or a decomposition product of a neutral complex of a cyclic silane. The content of the impurities in the neutral complex composition of a cyclic silane is preferably not more than 10% by mass, more preferably not more than 5% by mass, and the lower limit is, for example, 0.01% by mass, but may be 0% by mass.

Next, the method for manufacturing a cyclic hydrogenated silane or a cyclic organic silane of the present invention is described.

The method for manufacturing a cyclic hydrogenated silane of the present invention includes a reduction step of reducing the neutral complex of a cyclic silane of the pattern 2 obtained in the manufacturing method of the present invention. However, the neutral complex of a cyclic silane of the pattern 1 of the present invention is also useful as an intermediate for synthesizing the cyclic hydrogenated silane or the cyclic organic silane, and the cyclic hydrogenated silane or the cyclic organic silane may be produced by using the neutral complex of a cyclic silane of the pattern 1. By reducing the neutral complex of a cyclic silane in the reduction step, a cyclic hydrogenated silane can be obtained while the production of the by-product silane gas is suppressed.

The neutral complex of a cyclic silane of the present invention is neutral, and therefore is high in solubility in a solvent. Thus, conveniently, a reduction, alkylation or arylation reaction can be conducted in a homogeneous solution state or in a suspension high in dispersibility.

Further, the by-product silane gas is not produced, or only a small amount of the silane gas is produced during these reactions. Thus, a combustion facility and an adsorption facility as countermeasures against silane gas and organic monosilane, which have conventionally been used in the production of a cyclic hydrogenated silane or a cyclic organic silane, can be eliminated or simplified, and a countermeasure of dilution of the generated gas with inert gas or a simple device such as a scrubber is sufficient.

The reducing agent that can be used in the reduction step is not particularly limited, but one or more reducing agents selected from the group consisting of aluminum-based reducing agents and boron-based reducing agents are preferably used. Examples of the aluminum-based reducing agent include metal hydrides such as lithium aluminum hydride (LiAlH$_4$; LAH), diisobutyl aluminum hydride (DIBAL) and bis(2-methoxyethoxy) aluminum sodium hydride ("Red-Al" (registered trade mark of Sigma-Aldrich Corporation). Examples of the boron-based reducing agent include metal hydrides such as sodium borohydride and lithium triethylborohydride, and diborane. For example, in order to obtain a hydrogenated silane compound such as cyclohexasilane, a metal hydride may be used as the reducing agent. The reducing agents may be used alone or in combination of two or more thereof.

Further, a Lewis acid catalyst may be used as a reduction auxiliary in combination with the above reducing agents. The Lewis acid catalyst may be metal halide compounds including chlorides such as aluminum chloride, titanium chloride, zinc chloride, tin chloride and iron chloride; bromides such as aluminum bromide, titanium bromide, zinc bromide, tin bromide and iron bromide; iodides such as aluminum iodide, titanium iodide, zinc iodide, tin iodide and iron iodide; and fluorides such as aluminum fluoride, titanium fluoride, zinc fluoride, tin fluoride and iron fluoride. These Lewis acid catalysts may be used alone or in combination of two or more thereof.

The method for manufacturing a cyclic organic silane of the present invention includes a step of alkylating or arylating the neutral complex of a cyclic silane obtained in the manufacturing method of the present invention. In such a step of introducing an organic group onto a silicon atom, for example, alkylation or arylation of a neutral complex of a cyclic silane can give cyclic organic silanes such as dodecamethylcyclohexasilane while the generation of organic monosilane is suppressed. The dodecamethylcyclohexasilane is produced by the same reaction as the above methylation reaction conducted when the yield and yield constant of the neutral complex of a cyclic silane are measured.

The alkylating agent or the arylating agent that can be used in the step of alkylation or arylation is not particularly limited, but one or more agents selected from the group consisting of Grignard reagents and organolithium reagents are preferably used. Examples of the Grignard reagent include alkyl magnesium halides such as methyl magnesium bromide, and aryl magnesium halides such as phenyl magnesium bromide. Examples of the organic lithium reagent include alkyl lithium compounds such as methyl lithium, n-butyl lithium, sec-butyl lithium and tert-butyl lithium, and aryl lithium compounds such as phenyl lithium. The alkylating agent or the arylating agent may be used alone or in combination of two or more thereof.

Hereinafter, the method for manufacturing a cyclic hydrogenated silane of the present invention is mainly described. In the method for manufacturing a cyclic organic silane of the present invention, the terms "reducing agent" and "cyclic hydrogenated silane" in the description of the method for manufacturing a cyclic hydrogenated silane below are read as an "alkylating agent or arylating agent" and a "cyclic organic silane," respectively, and thus the description of the method for manufacturing a cyclic hydrogenated silane is appropriately applied to the method for manufacturing a cyclic organic silane.

As a method for reducing a neutral complex of a cyclic silane (e.g. [PPh$_3$]$_2$[Si$_6$Cl$_{12}$]) to obtain a cyclic hydrogenated silane (e.g. cyclohexasilane), for example, when LiAlH4 is used as a reducing agent, the scheme is represented as follows.

[Chemical Formula 3]

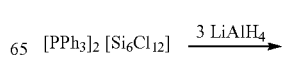

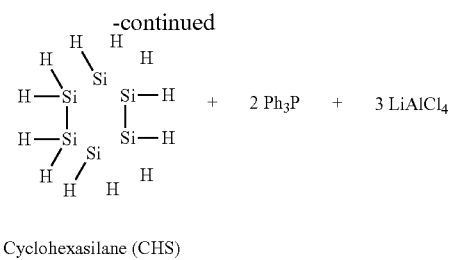

Cyclohexasilane (CHS)

The amount of the reducing agent to be used in the reduction step may be appropriately set. For example, the hydride equivalent in the reducing agent relative to one silicon-halogen bond in the neutral complex of a cyclic silane is preferably set to at least 0.9. The equivalent is more preferably set to 0.9 to 50, further preferably 0.9 to 30, particularly preferably 0.9 to 15, most preferably 0.9 to 2. When the amount of the reducing agent to be used is too large, the time required for a post-treatment tends to increase, resulting in reduction in productivity, whereas when the amount is too small, the yield tends to decrease.

The reduction reaction can be carried out in the presence of an organic solvent as necessary. Examples of the organic solvent that can be used hydrocarbon-based solvents such as hexane and toluene; and ether-based solvents such as diethyl ether, tetrahydrofuran, cyclopentyl methyl ether, diisopropyl ether, and methyl tertiary butyl ether. These organic solvents may be used alone or in combination of two or more thereof. The organic solvent solution obtained in the production of the neutral complex of a cyclic silane may be directly used as an organic solvent solution in the reduction step, or an organic solvent may be distilled off from an organic solvent solution containing the neutral complex of a cyclic silane and a newly added organic solvent may be used in the reduction step. Here, the organic solvent to be used in the reduction reaction is preferably subjected to purification such as distillation or dehydration before the reaction for removing water and dissolved oxygen contained therein.

As the amount of the organic solvent to be used in the reduction reaction, the concentration of the neutral complex of a cyclic silane is preferably adjusted to 0.01 to 1 mol/L, more preferably to 0.02 to 0.7 mol/L, and further preferably to 0.03 to 0.5 mol/L. When the concentration of the neutral complex of a cyclic silane is more than 1 mol/L, that is, when the amount of the organic solvent to be used is too small, the heat generated by the reduction reaction cannot be removed adequately and a reactant does not dissolve easily. This may possibly cause problems such as a decrease in reaction rate. On the other hand, when the concentration of the neutral complex of a cyclic silane is less than 0.01 mol/L, that is, when the amount of the organic solvent to be used is too large, the amount of the solvent to be distilled off increases when the organic solvent and an object product are separated from each other after the reduction reaction so that the productivity tends to decrease.

The reduction can be carried out by bringing the neutral complex of a cyclic silane into contact with the reducing agent. When the neutral complex of a cyclic silane is brought into contact with the reducing agent, the contact is preferably carried out in the presence of a solvent. In order to contact the neutral complex of a cyclic silane with the reducing agent in the presence of the solvent, for example, (1) the reducing agent is directly added to a solution or a dispersion liquid of the neutral complex of a cyclic silane, (2) a solution or a dispersion liquid obtained by dissolving or dispersing the reducing agent in the solvent is added to a solution or a dispersion liquid of the neutral complex of a cyclic silane, (3) the neutral complex of a cyclic silane and the reducing agent are simultaneously or sequentially added to the solvent, and the like may be adopted. Among them, the embodiment (2) is particularly preferable.

Also, when the neutral complex of a cyclic silane is brought into contact with the reducing agent, it is preferred that at least one of the neutral complex of a cyclic silane and the reducing agent be added dropwise to the reaction system in which the reduction is carried out. One or both of the neutral complex of a cyclic silane and the reducing agent are added dropwise as described above, whereby exothermic generated in the reduction reaction can be controlled by the dropwise addition rate or the like, thus an effect of leading to improved productivity can be obtained such that it is possible to downsize a condenser or the like.

The preferred embodiment when one or both of the neutral complex of a cyclic silane and the reducing agent are added dropwise includes the following three embodiments. That is, A) an embodiment in which a solution or dispersion of the neutral complex of a cyclic silane is charged in the reactor, and a solution or dispersion of the reducing agent is added dropwise thereto, B) an embodiment in which a solution or dispersion of the reducing agent is charged in the reactor, and a solution or dispersion of the neutral complex of a cyclic silane is added dropwise thereto, and C) an embodiment in which a solution or dispersion of the neutral complex of a cyclic silane and a solution or dispersion of the reducing agent are simultaneously or sequentially added dropwise to the reactor. Among them, the embodiment A) is preferable.

When one or both of the neutral complex of a cyclic silane and the reducing agent are added dropwise by the embodiments A) to C), the concentration in the solution or dispersion containing the neutral complex of a cyclic silane is preferably not less than 0.01 mol/L, more preferably not less than 0.02 mol/L, further preferably not less than 0.04 mol/L, and particularly preferably not less than 0.05 mol/L. When the concentration of the neutral complex of a cyclic silane is too low, the amount of the solvent that needs to be removed by distillation when isolating the objective product is increased, and thus the productivity tends to be lowered. On the other hand, the upper limit of the concentration in the solution or dispersion containing the neutral complex of a cyclic silane is preferably not more than 1 mol/L, more preferably not more than 0.8 mol/L, further preferably not more than 0.7 mol/L, and particularly preferably not more than 0.5 mol/L.

The lower limit of the temperature during dropwise addition (specifically, the temperature of a solution or a dispersion liquid during dropwise addition) is preferably $-198°$ C., more preferably $-160°$ C., further preferably $-100°$ C. The upper limit of the temperature during dropwise addition is preferably $+150°$ C., more preferably $+80°$ C., further preferably $-10°$ C., particularly preferably $-60°$ C. The temperature of a reaction container (reaction solution) (reaction temperature) may be appropriately set according to the types of a neutral complex of a cyclic silane and a reducing agent, and generally, the lower limit is preferably set to $-198°$ C., more preferably $-160°$ C., further preferably $-100°$ C. The upper limit of the temperature of a reaction container (reaction solution) is preferably $+150°$ C., more preferably $+80°$ C., further preferably $-10°$ C., particularly preferably $-60°$ C. When the reaction temperature is low, the decomposition or polymerization of an intermediate product or an object product can be suppressed, resulting in improvement of yield. The reaction time may be properly determined depending on the extent of reaction progress, and is usually not less than 10 minutes and not more than 72 hours, preferably not less than 1 hour and not more than 48 hours, and more preferably not less than 2 hours and not more than 24 hours.

It is preferred that the reduction reaction be usually carried out under an atmosphere of an inert gas such as nitrogen gas or argon gas. In the reaction in this reduction step, the generation of silane gas is suppressed. Therefore, a combustion facility and an adsorption facility as countermeasures against silane gas are unnecessary or can be simplified in the step. Further, a countermeasure can be taken by dilution of the generated gas with inert gas or a simple facility such as a scrubber, and a cyclic hydrogenated silane can be produced efficiently with a simple device.

The cyclic hydrogenated silane produced in the reduction reaction can be isolated by, for example, subjecting the reaction liquid obtained after the reduction to solid-liquid separation to separate a solid (impurities such as a salt as a by-product), and then distilling off the solvent under reduced pressure. As a method of solid-liquid separation, filtration is preferably employed for its simpleness, but the method is not limited thereto, and common solid-liquid separation methods such as centrifugation and decantation can be appropriately employed.

EXAMPLES

The present invention will be more specifically described below with reference to Examples, but the present invention is not limited to the following Examples, and can be implemented with appropriate modifications within the scope conforming to the purport of what is mentioned above and below herein. All of such modifications are included in the technical scope of the present invention.

Here, all reactions in Examples were carried out under an inert gas (nitrogen or argon) atmosphere. Also, solvents used in the reaction in Examples were used after water and oxygen were removed.

Example 1

The inside of a 300-mL four-necked flask equipped with a thermometer, a condenser, a dropping funnel and a stirrer was replaced with nitrogen gas, and 5.81 g (0.022 mol) of triphenylphosphine as a coordination compound, 17.2 g (0.133 mol) of diisopropylethylamine (DIPEA) as a tertiary amine and 100 mL of 1,2-dichloroethane as a solvent were then charged therein, to prepare a solution. Subsequently, while the solution in the flask was stirred, 18.0 g (0.133 mol) of trichlorosilane as a halosilane compound was slowly added dropwise from the dropping funnel in the condition of 25° C. After the completion of dropwise addition, the reaction was carried out by continuously stirring the mixture for 2 hours and subsequently heating and stirring the mixture at 60° C. for 8 hours to give a homogeneous reaction solution. The resultant reaction solution was condensed and washed to give a neutral reaction product as a white solid, containing dodecachlorocyclohexasilane to which triphenylphosphine is coordinated ([PPh$_3$]$_2$[Si$_6$Cl$_{12}$]). The yield was 36%. It was made evident that the complex obtained in the cyclization reaction shows high solubility in a solvent.

The cyclization reaction proceeded according to the following scheme, and a neutral complex of dodecachlorocyclohexasilane to which triphenylphosphine was coordinated was produced.

[Chemical Formula 4]

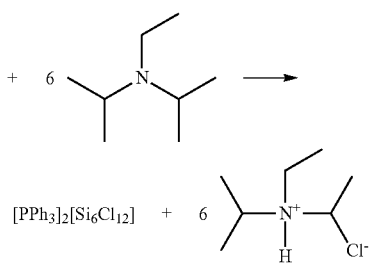

Figure 2:
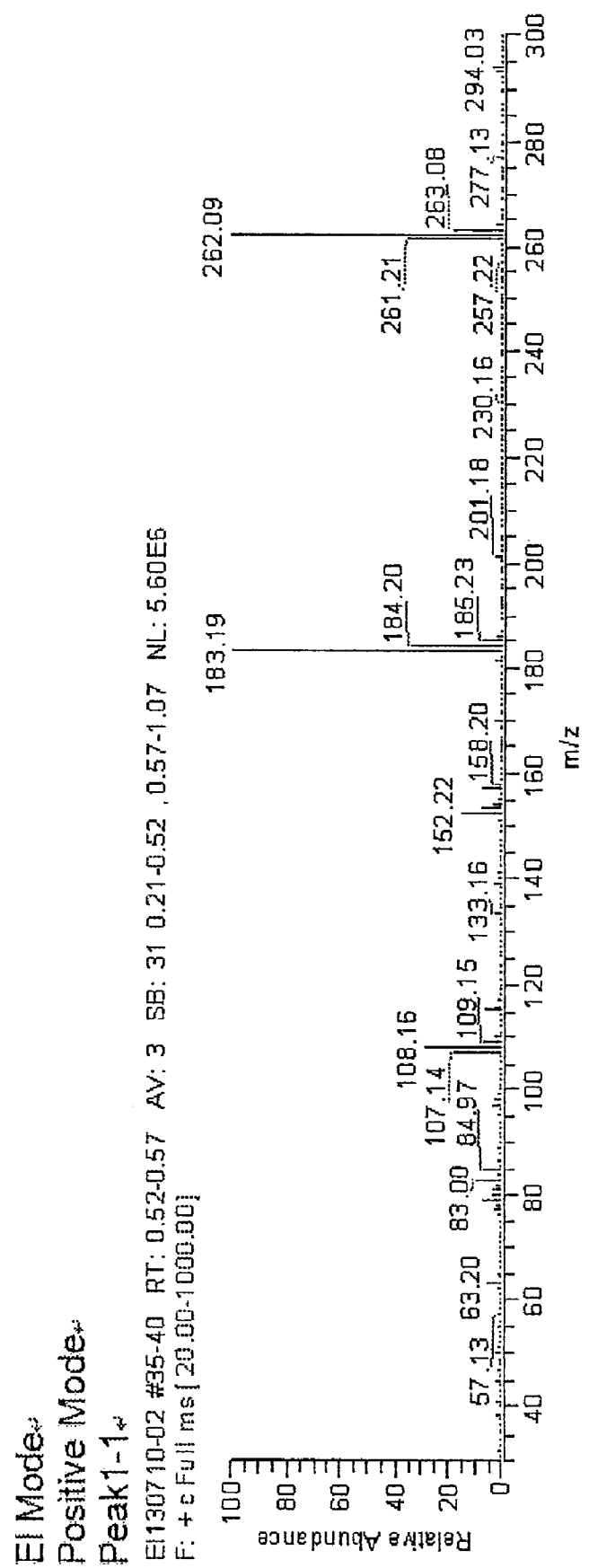
FIG. 2 shows a result of mass spectrometry of the neutral complex of a cyclic silane obtained in Example 1 in a cation measurement mode.

A mass spectrometry (MS) result of the purified product, which was obtained by an electron ionization (EI) method, is shown in FIG. 1. In FIG. 1, only one peak appeared at a position of 0.55 min. A result obtained by measuring this peak in a cation measurement mode is shown in FIG. 2. A peak at 262.09 m/z is a peak of triphenylphosphine, and no peaks of diisopropylethylamine, diisopropylethylamine hydrochloride and a quaternary phosphonium salt were observed. The mass spectrometry was conducted with a gas chromatograph mass spectrometer (PolarisQ; manufactured by Thermoequst).

Figure 3:
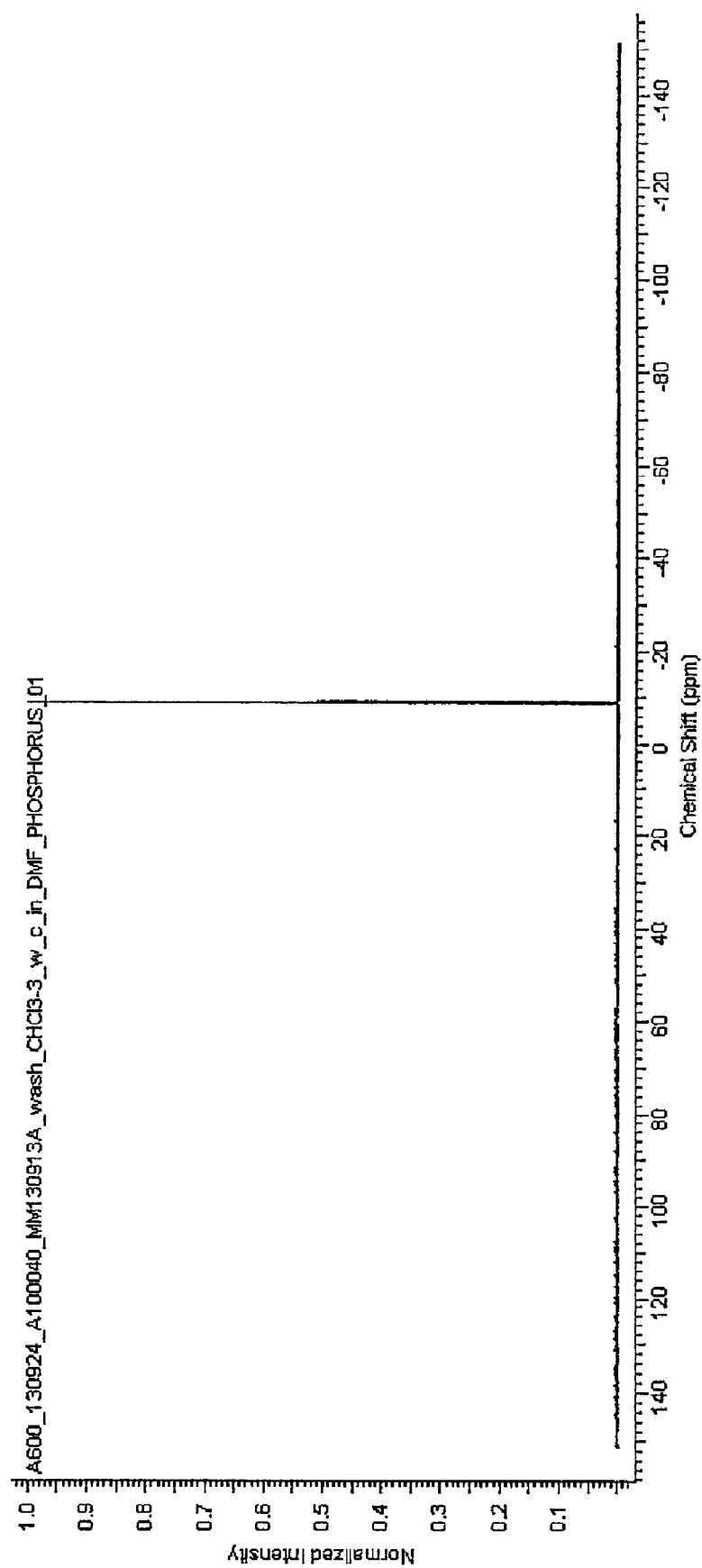
FIG. 3 shows a measurement result of $^{31}$P-NMR of the neutral complex of a cyclic silane obtained in Example 1.

A measurement result of $^{31}$P-NMR is shown in FIG. 3. The peak obtained is one for a triphenylphosphine ligand, and it was confirmed that a phosphorus compound other than triphenylphosphine was not present because no other peak was obtained. The measurement of $^{31}$P-NMR was carried out at 600 MHz in deuterated dimethylformamide (DMF-d7) using a NMR manufactured by Varian, Inc.

Figure 4:
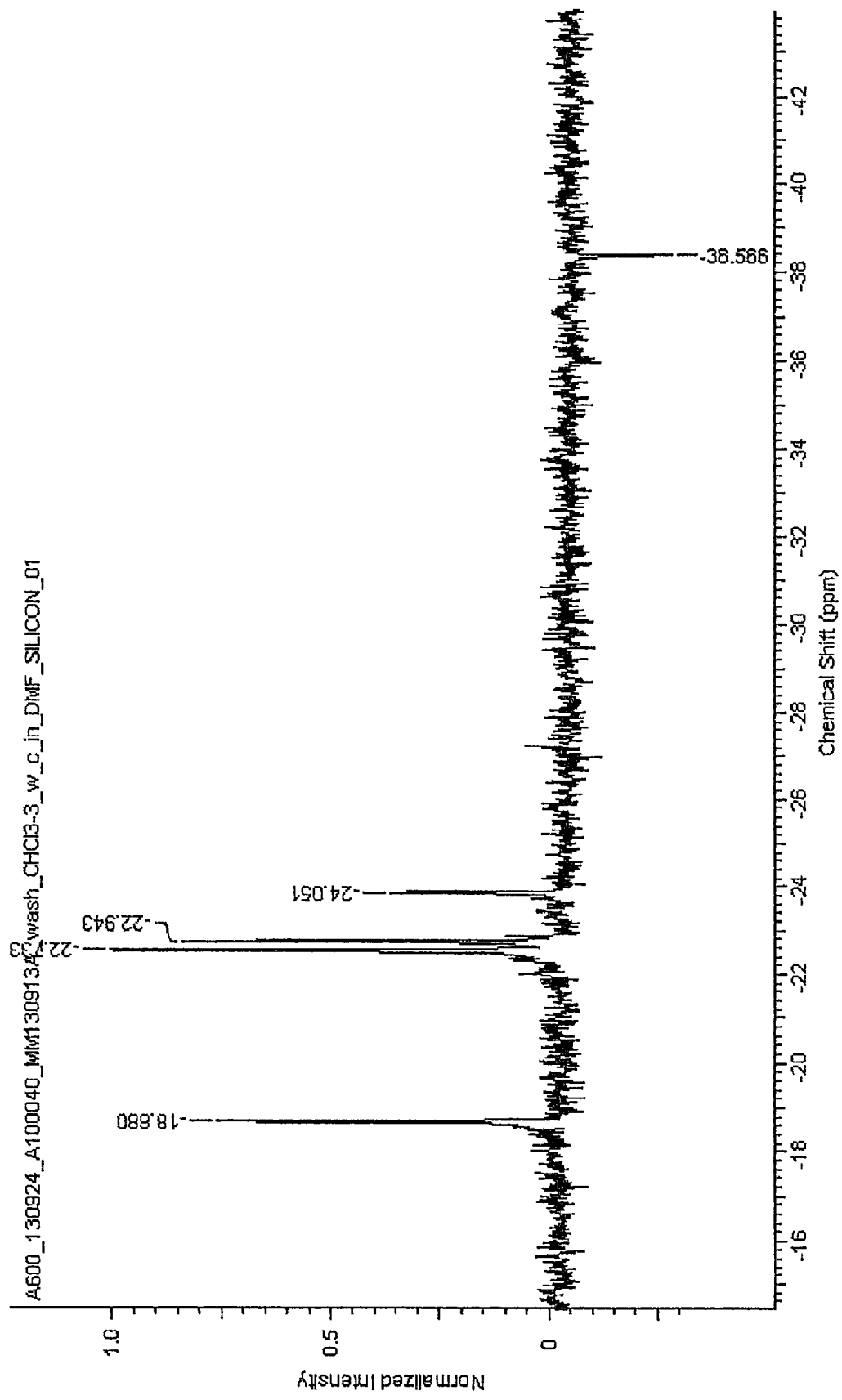
FIG. 4 shows a measurement result of $^{29}$Si-NMR of the neutral complex of a cyclic silane obtained in Example 1.

A measurement result of $^{29}$Si-NMR is shown in FIG. 4. A signal at-22.733 ppm is a signal of Si$_6$Cl$_{12}$, and it was confirmed that Si$_6$HCl$_{11}$ was also mixed in the purified product due to the presence of the remaining 4 signals. The Si$_6$HCl$_{11}$ will turn into Si$_6$H$_{12}$ in the next reduction step, and therefore, separation is not particularly needed.

The measurement result of $^{29}$Si-NMR (600 MHz, DMF-d7);
Si$_6$Cl$_{12}$; −22.73 ppm
Si$_6$HCl$_{11}$: δ−18.89, −22.94, −24.05, −38.56 ppm
Measurement was carried out also in $^1$H-NMR (600 MHz, DMF-d7).
The measurement result ; δ7.56, 7.46 ppm.

These results are summed up that the compound obtained in Example 1 was a mixture containing a neutral complex including triphenylphosphine coordinated to dodecachlorocyclohexasilane ([PPh$_3$]$_2$[Si$_6$Cl$_{12}$]) and [PPh$_3$]$_2$[Si$_6$HCl$_{11}$].

It was made evident that the structure of dodecachlorocyclohexasilane does not contain any silane atom other than the silane atoms that form the ring structure, and therefore, the generation of silane gas and the like is suppressed in the reduction.

Example 2

In a 100-mL two-necked flask equipped with a dropping funnel and a stirrer was charged 2.44 g of the white solid obtained in Example 1 (dodecachlorocyclohexasilane-containing reaction product, 2.18 mmol), and the white solid was dried under reduced pressure. Then, the inside of the flask was replaced with argon gas, and 30 mL of cyclopentyl methyl ether (CPME) was added as a solvent. Subsequently, while the suspension in the flask was stirred, 10 mL of a solution of lithium aluminum hydride (LiAlH$_4$) in diethyl ether (concentration: about 1.0 mol/L) was gradually added dropwise as a reducing agent from the dropping funnel under the condition of −20° C., and then the reaction was carried out by stirring the mixture at −20° C. for 5 hours.

After the reaction, the reaction liquid was filtered under a nitrogen atmosphere to remove a produced salt. The solvent was distilled off from the obtained filtrate under reduced pressure to give a colorless transparent liquid of crude cyclohexasilane at a yield of 62%. The reduction reaction is considered to have proceeded according to the following scheme. The purified cyclohexasilane obtained by subjecting this crude cyclohexasilane to distillation purification had a 99 area % of cyclohexasilane as a result of gas chromatography analysis. In addition, the purity of the purified cyclohexasilane was 99% when determined from the results of $^1$H-NMR (400 MHz; $C_6D_6$) and $^{29}$Si-NMR (400 MHz; $C_6D_6$).

$^1$H-NMR (400 MHz; $C_6D_6$) δ 6 3.35 ppm, $^{29}$Si-NMR (400 MHz; $C_6D_6$) δ −106.9 ppm

[Chemical Formula 5]

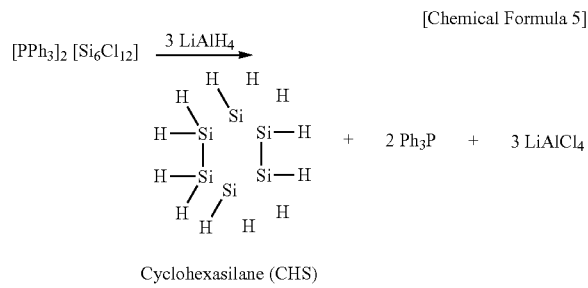

Cyclohexasilane (CHS)

Example 3

A reduction step was carried out using the purified product of the neutral complex of a cyclic silane obtained in Example 1. In a flask was charged 204 mg of LiAlH$_4$ and 10 g of cyclopentyl methyl ether (CPME) under a nitrogen atmosphere, and the mixture was stirred at room temperature for 1 hour to prepare a slurry of LiAlH4. In another 100-mL flask was charged 2.0 g of the purified product obtained in Example 1 and 70 g of CPME under an argon atmosphere, and the mixture was stirred at −60° C. The slurry of LiAlH4 was added dropwise thereto from a dropping funnel over 10 minutes. After the completion of the dropwise addition, the resultant mixture was stirred at −60° C. for 6 hours.

After the completion of the reaction, the reaction liquid was filtered using a glass filter with a micropore size of 20 to 30 μm under a nitrogen atmosphere, and the solvent was distilled off from the obtained filtrate under reduced pressure to give a colorless transparent liquid of crude cyclohexasilane (yield 80%). The purified cyclohexasilane obtained by subjecting this crude cyclohexasilane to distillation purification had a 99 area % of cyclohexasilane as a result of gas chromatography analysis. In addition, the purity of the purified cyclohexasilane was 99% when determined from the results of $^1$H-NMR (400 MHz; $C_6D_6$) and $^{29}$Si-NMR (400 MHz; $C_6D_6$). In the present reaction, the equivalent of the hydride (5.4 mmol×4=21.6 mmol) relative to the Si—Cl bond (1.8 mmol×12=21.6 mmol) in the complex was 1.0.

$^1$H-NMR (400 MHz; $C_6D_6$) δ 3.35 ppm, $^{29}$Si-NMR (400 MHz; $C_6D_6$) δ −106.9 ppm Example 4

Synthesis of a neutral complex of a cyclic silane was carried out in the same manner as in Example 1 except that the coordination compound was changed as follows. The yield was 20% with triphenylphosphine oxide (PH$_3$P=O), 42% with tris(4-methoxyphenyl)phosphine (P(MeOPh)$_3$), 15% with p-tolunitrile, 8% with diisopropylethylamine, and 20% with pyridine.

Example 5

In a 500-mL separable flask equipped with a dropping funnel and a stirrer was charged 32.9 g of the white solid obtained in Example 1 (dodecachlorocyclohexasilane-containing reaction product, 29.8 mmol), and the white solid was dried under reduced pressure. Then, the inside of the flask was replaced with argon gas, and 235 mL of cyclopentyl methyl ether (CPME) was added as a solvent. Subsequently, while the suspension in the flask was stirred, 90 mL of a solution of lithium aluminum hydride (LiAlH$_4$) in diethyl ether (concentration: about 1.0 mol/L) was gradually added dropwise as a reducing agent from the dropping funnel under the condition of −60° C., and then the reaction was carried out by stirring the mixture at −60° C. for 3 hours. The monosilane gas produced as a by-product during the reaction was monitored with the silane gas sensor X-am 7000 manufactured by Drägerwerk Safety AG & Co. The total discharge amount of monosilane during the reaction was 0.09 mmol. After the completion of the reaction, the reaction liquid was filtered under pressure under a nitrogen atmosphere to remove a produced salt. The yield of the crude cyclohexasilane was 70% as a result of gas chromatography analysis of the filtrate. In the present reaction, the equivalent of the hydride (90 mmol×4=360 mmol) relative to the Si—Cl bond (29.8 mmol×12=357.6 mmol) in the complex was 1.0.

Example 6

In a 100-mL two-necked flask equipped with a dropping funnel and a stirrer was charged 2.0 g of the white solid obtained in Example 1 (dodecachlorocyclohexasilane-containing reaction product, 1.8 mmol), and the white solid was dried under reduced pressure. Then, the inside of the flask was replaced with argon gas, and 94 mL of cyclopentyl methyl ether (CPME) was added as a solvent. Subsequently, while the suspension in the flask was stirred, 11 mL of a solution of lithium aluminum hydride (LiAlH$_4$) in diethyl ether (concentration: about 1.0 mol/L) was gradually added dropwise as a reducing agent from the dropping funnel under the condition of −60° C., and then the reaction was carried out by stirring the mixture at −60° C. for 3 hours.

After the completion of the reaction, the reaction liquid was filtered using a glass filter with a micropore size of 20 to 30 μm under a nitrogen atmosphere, and the solvent was distilled off from the obtained filtrate under reduced pressure to give a colorless transparent liquid of crude cyclohexasilane (yield 65%). In the present reaction, the equivalent of the hydride (11 mmol×4=44 mmol) relative to the Si—Cl bond (1.8 mmol×12=21.6 mmol) in the complex was 2.0.

Industrial Applicability

The neutral complex of a cyclic silane of the present invention is useful as an intermediate for synthesizing cyclic hydrogenated silanes such as cyclohexasilane, or cyclic organic silanes such as dodecamethylcyclohexasilane. The neutral complex of a cyclic silane is excellent in solubility, and therefore, a cyclization reaction for synthesizing a neutral complex of a cyclic halosilane and a synthesis reaction for a cyclic hydrogenated silane or a cyclic organic silane can be conducted in the state of a homogeneous solution or a suspension high in dispersibility. The cyclic hydrogenated silane is useful as a silicon material used for, for example, solar cells or semiconductors. Further, in the semiconductor field, the cyclic hydrogenated silane can also be used for production of SiGe compounds or SiGe films by mixing or reacting the cyclic hydrogenated silane with a Ge compound.

The invention claimed is:

1. A neutral complex of a cyclic silane represented by the general formula $$[Y]_l[Si_m Z_{2m-a} H_a],$$

wherein Y is at least one coordination compound selected from the group consisting of (1) a compound represented as $X^1 R^1{}_n$ (when $X^1$ is P, P=O or N, n=3 and each $R^1$ represents a substituted or unsubstituted alkyl group or aryl group and $R^1$s are the same or different; when $X^1$ is S, S=O or O, n=2 and each $R^1$ represents the same group as described above and $R^1$s are the same or different; and the number of amino groups in $X^1 R^1{}_n$ is 0 or 1), and (2) at least one heterocyclic compound selected from the group consisting of substituted or unsubstituted N—, O—, S— or P— containing heterocyclic compounds that have an unshared electron pair in the ring (the number of amino groups in the heterocyclic compound is 0 or 1), each Z represents a halogen atom of any of Cl, Br, I and F and Zs are the same or different, l is 1 or 2, m is 3 to 8, and a is 0 to m.

2. The neutral complex of a cyclic silane according to claim 1, wherein Y in the general formula is at least one compound selected from the group consisting of $PR_3$ and a substituted or unsubstituted N— containing heterocyclic compound having an unshared electron pair in the ring.

3. The neutral complex of a cyclic silane according to claim 1, wherein the neutral complex of a cyclic silane contains $[Y]_l[Si_6 Cl_{12}]$ (l is 1 or 2).

4. The neutral complex of a cyclic silane according to claim 1, the neutral complex of a cyclic silane being an intermediate for synthesizing a cyclic hydrogenated silane or a cyclic organic silane.

5. A method for manufacturing a neutral complex of a cyclic silane, comprising a step of conducting a cyclization reaction of a halosilane compound in the presence of at least one coordination compound selected from the group consisting of the following (3) and (4):

(3) a compound represented as $X^2 R^2{}_q$ (when $X^2$ is P or P=O, q=3 and each $R^2$ represents a substituted or unsubstituted alkyl group or aryl group and $R^2$s are the same or different; when $X^2$ is S, S=O or O, q=2 and each $R^2$ represents a substituted or unsubstituted alkyl group or aryl group and $R^2$s are the same or different; when $X^2$ is CN, q=1 and $R^2$ represents a substituted or unsubstituted alkyl group or aryl group; and the number of amino groups in $X^2 R^2{}_q$ is 0 or 1); and (4) at least one heterocyclic compound selected from the group consisting of substituted or unsubstituted N—, O—, S— or P— containing heterocyclic compounds that have an unshared electron pair in the ring (the number of amino groups in the heterocyclic compound is 0 or 1).

6. The method for manufacturing a neutral complex of a cyclic silane according to claim 5, wherein the cyclization reaction is conducted in the presence of a tertiary amine (except a tertiary polyamine).

7. The method for manufacturing a neutral complex of a cyclic silane according to claim 5, wherein the neutral complex of a cyclic silane contains a neutral complex of dodecachlorocyclohexasilane including the coordination compound(s) coordinated to dodecachlorocyclohexasilane.

8. A method for manufacturing a cyclic hydrogenated silane, comprising a step of reducing the neutral complex of a cyclic silane obtained in the manufacturing method according to claim 5.

9. The method for manufacturing a cyclic hydrogenated silane according to claim 8, wherein at least one reducing agent selected from the group consisting of an aluminum-based reducing agent and a boron-based reducing agent is used as a reducing agent in the reduction step.

10. The method for manufacturing a cyclic hydrogenated silane according to claim 8, wherein the hydride equivalent in the reducing agent relative to one silicon-halogen bond in the neutral complex of a cyclic silane is 0.9 to 2.0 in the reduction step.

11. The method for manufacturing a cyclic hydrogenated silane according to claim 8, wherein the reduction step is conducted at −198° C. to −10° C.

12. A method for manufacturing a cyclic organic silane, comprising a step of alkylating or arylating the neutral complex of a cyclic silane obtained by the manufacturing method according to claim 5 with at least one reagent selected from the group consisting of a Grighard reagent and an organolithium reagent.

13. The method for manufacturing a neutral complex of a cyclic silane according to claim 5, wherein an amount of the coordination compound is at least 2.0 mol and up to 50 mol relative to 6 mol of the halosilane compound.

* * * * *